(12) United States Patent
Parris et al.

(10) Patent No.: US 8,878,257 B2
(45) Date of Patent: Nov. 4, 2014

(54) METHODS AND APPARATUS FOR AN ISFET

(75) Inventors: Patrice M. Parris, Phoenix, AZ (US);
Weize Chen, Phoenix, AZ (US);
Richard J. De Souza, Chandler, AZ (US); Md M. Hoque, Gilbert, AZ (US);
John M. McKenna, Chandler, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 362 days.

(21) Appl. No.: 12/794,591

(22) Filed: Jun. 4, 2010

(65) Prior Publication Data

US 2011/0299337 A1    Dec. 8, 2011

(51) Int. Cl.
| | |
|---|---|
| *G01N 27/414* | (2006.01) |
| *H01L 27/115* | (2006.01) |
| *H01L 29/788* | (2006.01) |
| *H01L 29/94* | (2006.01) |
| *H01L 49/02* | (2006.01) |
| *G11C 16/04* | (2006.01) |
| *H01L 29/66* | (2006.01) |
| *H01L 23/522* | (2006.01) |

(52) U.S. Cl.
CPC .......... *H01L 29/94* (2013.01); *H01L 27/11526* (2013.01); *H01L 29/788* (2013.01); *G01N 27/4148* (2013.01); *H01L 27/11558* (2013.01); *H01L 28/60* (2013.01); *H01L 23/5223* (2013.01); *G11C 16/0416* (2013.01); *H01L 29/66825* (2013.01)
USPC .. 257/253; 257/414; 257/E27.06; 257/E29.3; 324/71.5

(58) Field of Classification Search
CPC . H01L 29/788; G01N 27/414; G01N 27/4148
USPC ................. 365/185.18; 257/253, 414, E29.3, 257/E27.06; 438/49; 324/71.5
See application file for complete search history.

(56) References Cited

U.S. PATENT DOCUMENTS

| | | | |
|---|---|---|---|
| 7,462,512 B2 * | 12/2008 | Levon et al. | 438/123 |
| 7,535,232 B2 | 5/2009 | Barbaro et al. | |
| 2008/0094074 A1 | 4/2008 | Kim et al. | |

OTHER PUBLICATIONS

Milgrew, M.J., et al., Matching the Transconductance Characteristics of CMOS ISFET Arrays by Removing Trapped Charge, IEEE Trans. Elec. Dev., vol. 55, No. 4. pp. 1074-1079, Apr. 2008.
Georgiou, P., et al., CMOS-based programmable gate ISFET, Elec. Lett., vol. 44, No. 22, Oct. 2008.
Shen, N. Y., et al., The Chemoreceptive Neuron MOS Transistors (CvMOS): A Novel Floating-Gate Device for Molecular and Chemical Sensing, IEEE 12th Int. Conf. on Sol. St. Sens., Act. and MicroSys., pp. 69-72, Jun. 2003.

* cited by examiner

*Primary Examiner* — Allison P Bernstein
(74) *Attorney, Agent, or Firm* — Ingrassia Fisher & Lorenz, P.C.

(57) ABSTRACT

An ISFET includes a control gate coupled to a floating gate in a CMOS device. The control gate, for example, a poly-to-well capacitor, is configured to receive a bias voltage and effect movement of a trapped charge between the control gate and the floating gate. The threshold voltage of the ISFET can therefore by trimmed to a predetermined value, thereby storing the trim information (the amount of trapped charge in the floating gate) within the ISFET itself.

5 Claims, 7 Drawing Sheets

METHODS AND APPARATUS FOR AN ISFET

TECHNICAL FIELD

Embodiments of the subject matter described herein relate generally to semiconductor devices, and more particularly relate to Ion-Sensitive Field Effect Transistors (ISFETs).

BACKGROUND

Ion-Sensitive Field Effect Transistors (ISFETs) are often used, for example, to sense the ion concentration of an electrolytic solution. In early ISFET designs, the fluid being sensed was often in intimate contact with the gate dielectric, or separated from the gate dielectric by an ion-sensitive membrane. Ultimately, however, CMOS process flows were used to create relatively low-cost ISFET structures with improved manufacturability.

Known CMOS ISFETs, however, are unsatisfactory in a number of respects. For example, the threshold voltage (Vt) at neutral pH of such devices is known to vary widely. Furthermore, CMOS ISFETs are also prone to voltage drift during operation. These deleterious effects are primarily attributed to the presence of fixed charge within the gate dielectric (and/or passivation layers) as well as process-induced charges within the polysilicon floating gate. While standard UV-erase processes have been used to address part of this problem, the length of time required to remove the trapped charge is generally impractical in a mass-production environment.

Accordingly, there is a need for improved ISFET devices that exhibit improved, controllable Vt characteristics and which are manufacturable using conventional CMOS semiconductor processes.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The following description refers to elements or nodes or features being "connected" or "coupled" together. As used herein, unless expressly stated otherwise, "connected" means that one element is directly joined to (or directly communicates with) another element, and not necessarily mechanically. Likewise, unless expressly stated otherwise, "coupled" means that one element is directly or indirectly joined to (or directly or indirectly communicates with) another element, and not necessarily mechanically. Thus, although the schematic shown in the figures depict one exemplary arrangement of elements, additional intervening elements, devices, features, or components may be present in an embodiment of the depicted subject matter.

For the sake of brevity, conventional techniques related to semiconductor processing, CMOS devices, MOSFETs, ion-sensitive devices, and other functional aspects of the systems (and the individual operating components of the systems) may not be described in detail herein. Furthermore, the connecting lines shown in the various figures contained herein are intended to represent exemplary functional relationships and/or physical couplings between the various elements.

Technologies and concepts discussed herein generally relate to an ISFET design that allows charge to be moved to and from the ISFET floating gate structure, facilitating trimming and improving $V_t$ distribution. This movement of charge may be accomplished using, for example, one or more capacitors such as Metal-Oxide-Semiconductor (MOS) capacitors, metal-insulator-metal (MIM) capacitors, or the like, manufactured using standard CMOS processing techniques.

As mentioned in the Background, the threshold voltage (Vt) at neutral pH of prior art ISFET devices is known to vary widely. Furthermore, CMOS ISFETs are also prone to voltage drift during operation. These deleterious effects are primarily attributed to the presence of fixed charge within the gate dielectric (and/or passivation layers) as well as process-induced charges within the polysilicon floating gate. While standard UV-erase processes have been used to address part of this problem, the length of time required to remove the trapped charge is generally impractical in a mass-production environment.

Figure 1:
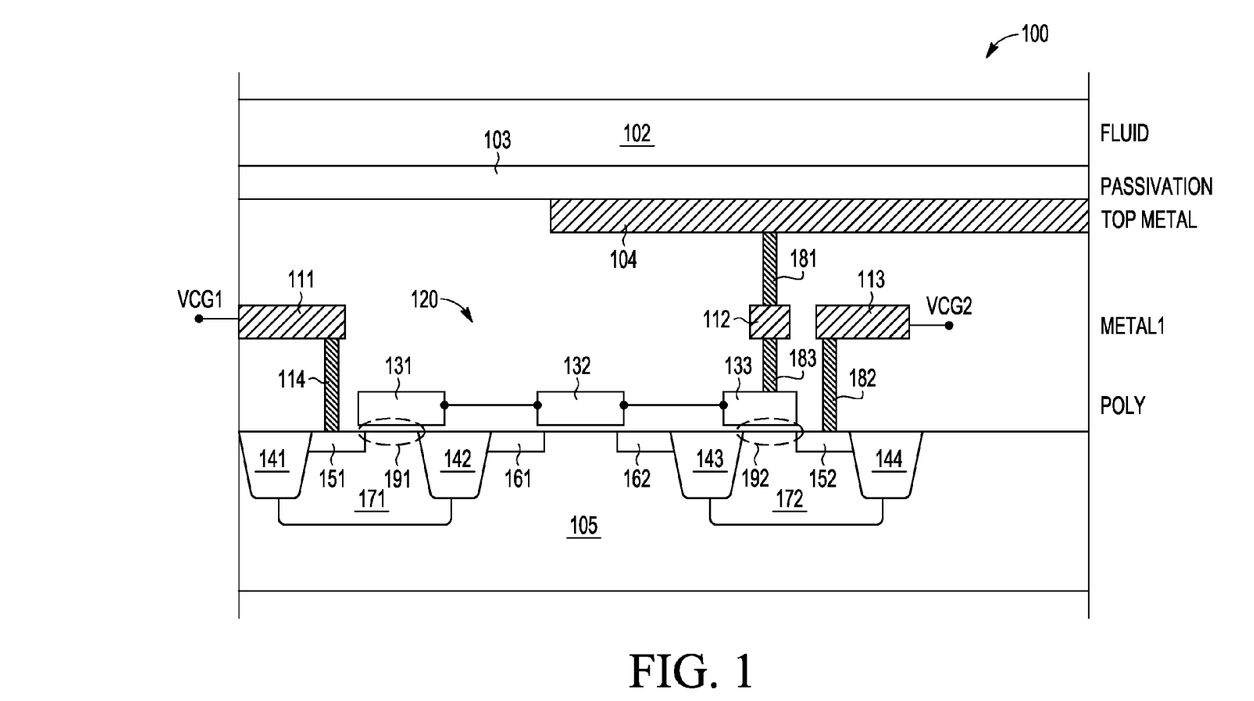
FIG. 1 is a conceptual cross-sectional view of an ISFET in accordance with one embodiment of the invention.

FIG. 1 depicts, in a conceptual cross-sectional view, an ISFET structure (or simply "ISFET") 100 in accordance with one embodiment. In general, wells 171 and 172 (e.g., n-wells) are formed within a semiconductor substrate 105 (e.g., a silicon, GaAs, or other such substrate), and are bordered by trenches 141, 142, 143, and 144 in the conventional manner. A MOSFET structure is formed by drain/source regions (e.g., regions of diffused impurities, or simply "diffusions") 161 and 162—and the channel region formed therebetween—acting in combination with a floating sense gate electrode (or simply "floating gate") 120 comprising gate electrode regions 131, 132, and 133, which are electrically coupled together in any suitable fashion. That is, for example, regions 131, 132, and 133 may consist of cross-sectional areas of conventional "fingers" of a contiguous polysilicon structure or other gate structure.

Gate electrode region 131 is formed above trench 142, well 171, and a well contact region 151. Similarly, gate electrode region 133 is formed above trench 143, well 172, and a well contact region 152. Well contact regions 151 and 152 may comprise, for example, regions of diffused impurities, as is known in the art. Control gate electrode 111 is coupled to well contact region 151 via an interconnect 114, and control gate electrode 113 is coupled to well contact region 152 via an interconnect 182. Thus, gate electrode region 131, well 171, and the oxide layer therebetween together form a poly-to-well capacitor 191. In this way, a capacitor structure is formed in part of the substrate 105. Similarly, gate electrode region 133, well 172, and an oxide layer therebetween (e.g., gate oxide) form a second poly-to-well capacitor 192. A sensor plate (or "sense plate") 104 is suitably coupled to a fluid layer 102 (e.g., the fluid being sensed) via one or more passivation layers 103 and one or more conductive structures. In the illustrated embodiment, electrical communication between fluid 102 and floating gate 120 is provided by a metal sense plate 104, interconnects (e.g., vias) 181 and 183, and a metal structure 112. Those skilled in the art will recognize that sense plate metal 104 will typically correspond to the "top metal" of a standard CMOS process, and likewise structures 111, 112, and 113 generally correspond to the "metal 1" of a standard CMOS process. The present embodiments are not limited, however, to a specific number of such metal layers.

In general, during operation of ISFET 100, the ion concentration within fluid 102 results in a corresponding electrical bias of floating gate 120. This bias results in MOS behavior vis-à-vis source and drain diffusions 161 and 162, generating a signal correlatable to the ion concentration of fluid 102. As noted earlier, however, the presence of process-induced charge within floating gate 120 can significantly affect the $V_t$ of the structure. Consequently, the electrical behavior of ISFET 100 (with respect to a given ion concentration of fluid 102) can be difficult to predict.

In accordance with the illustrated embodiments, however, by the application of an appropriate voltage to control gate electrode 111 (VCG1) and/or gate electrode 113 (VCG2), the trapped charge within floating gate 120 can be removed, via charge tunneling, through one of the two poly-to-well capacitors 191 and 192. In this way, the threshold voltage can be trimmed (during manufacturing, or after packaging) to a suitable value, while at the same time not significantly stressing the gate oxide (or other gate dielectric) below gate region 132.

In the illustrated embodiment of FIG. 1, for example, a positive bias VCG2 may be applied to control gate electrode 113 with respect to well 172, attracting electrons from floating gate 120, which then tunnel through the oxide below gate electrode region 133 to well 172 and ultimately to control gate electrode 113. This movement of charge results a net change in threshold voltage associated with floating gate 120 and the underlying FET structure. Similarly, a positive bias VCG1 may be applied to control gate electrode 111 to cause tunneling of electrons onto floating gate 120 through poly-to-well capacitor 192. This trimming step may be performed during manufacturing or later, during normal operation of the device.

In one embodiment, the two poly-to-well capacitors are substantially different in size such that a high electric field is created across the gate oxide in the smaller of the two capacitors, thereby forcing charge transfer at that location. The bias applied during this step (e.g., via an external DC voltage source) may vary depending upon, among other things, the thickness of the gate oxide and the overall geometry of the ISFET itself (e.g., as low as about 2.0 volts in some embodiments, and over 20.0 volts in others).

The ability to trim ISFET 100 by moving charge around within the device (e.g., on and off of floating gate 120) is particularly advantageous in that the required offset bias is effectively "stored" within the device. That is, the state of charge of the floating gate 120 can be viewed as the storage of information regarding the trim settings of ISFET 100. The illustrated embodiment therefore does not require a separate semiconductor device and/or chip to store calibration information necessary to trim the threshold voltage of ISFET 100 to a suitable level.

In general, trimming the threshold voltage of ISFET 100 proceeds as follows. First, the initial (e.g., as manufactured) threshold voltage value of ISFET 100 is determined. This may be accomplished, for example, using conventional test equipment capable of probing and measuring the threshold voltage of a FET. In the interest of clarity, the various test pads and the like used in connection with such tests are not shown in the figures.

After the initial threshold value is determined, a bias voltage is applied to the control gate electrodes 111 or 113 based on this threshold voltage such that at least a portion of charge within the ISFET migrates to the control gate connected to gate electrode 113. The applied bias voltage (e.g., 2.0-20V) may be modified, and the ISFET retested, until the ISFET has a threshold voltage that is substantially equal to a predetermined (e.g., target) threshold value for the device.

Figure 2:
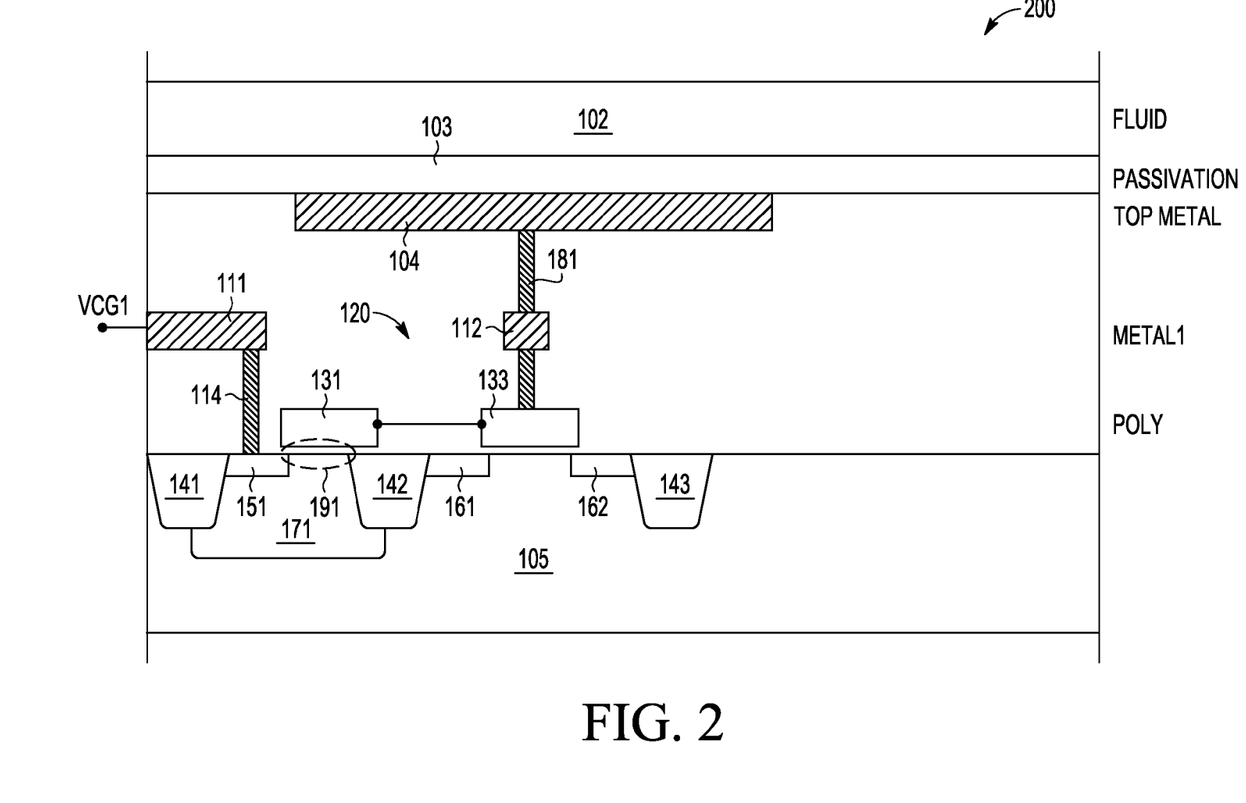
FIG. 2 is a conceptual cross-sectional view of an ISFET in accordance with an alternate embodiment of the invention.

FIG. 2 depicts an alternate embodiment of an exemplary ISFET 200. In this embodiment, a single poly-to-well capacitor 191 is used, rather than two such capacitors as illustrated in FIG. 1. The resulting structure is simplified, and can be similarly programmed by applying either a positive or negative bias to VCG1. To allow for both positive and negative bias on VCG1, well 171 is preferably isolated (e.g., through junction isolation) from substrate 105. As mentioned previously, the application of positive or negative bias may be performed during manufacturing or during normal operation of the device.

Figure 3:
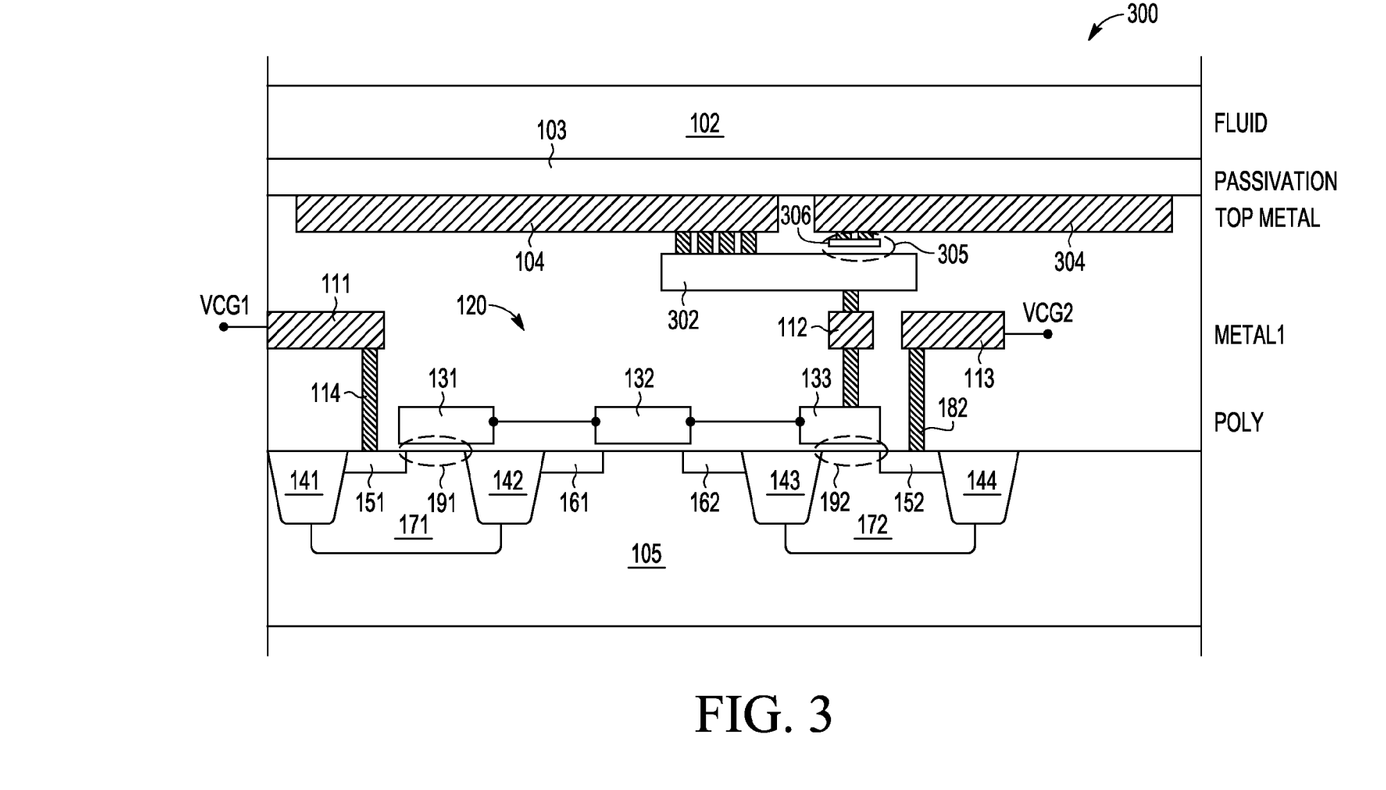
FIG. 3 is a conceptual cross-sectional view of an ISFET in accordance with an alternate embodiment of the invention.

FIG. 3 depicts an alternate embodiment of an exemplary ISFET 300. In this embodiment (comparing it to the embodiment shown in FIG. 1), a metal-insulator-metal (MIM) capacitor 305 is formed by a metal structure 306 (e.g., a top metal structure) a metal structure 302, and the dielectric formed therebetween. In this embodiment, poly-to-well capacitor 192 is optional, and need not be used. That is, positive biases may be applied to VCG1 or the top plate of MIM capacitor 305 to effect trimming. The structure and materials for MIM 305 may vary. In one embodiment, the bottom plate of MIM capacitor 305 is the 2nd-to-last metal layer, and the top plate could be any suitable conductor, such as TiN. The dielectric therebetween may be a nitride, oxide, or a combination thereof.

Figure 4:
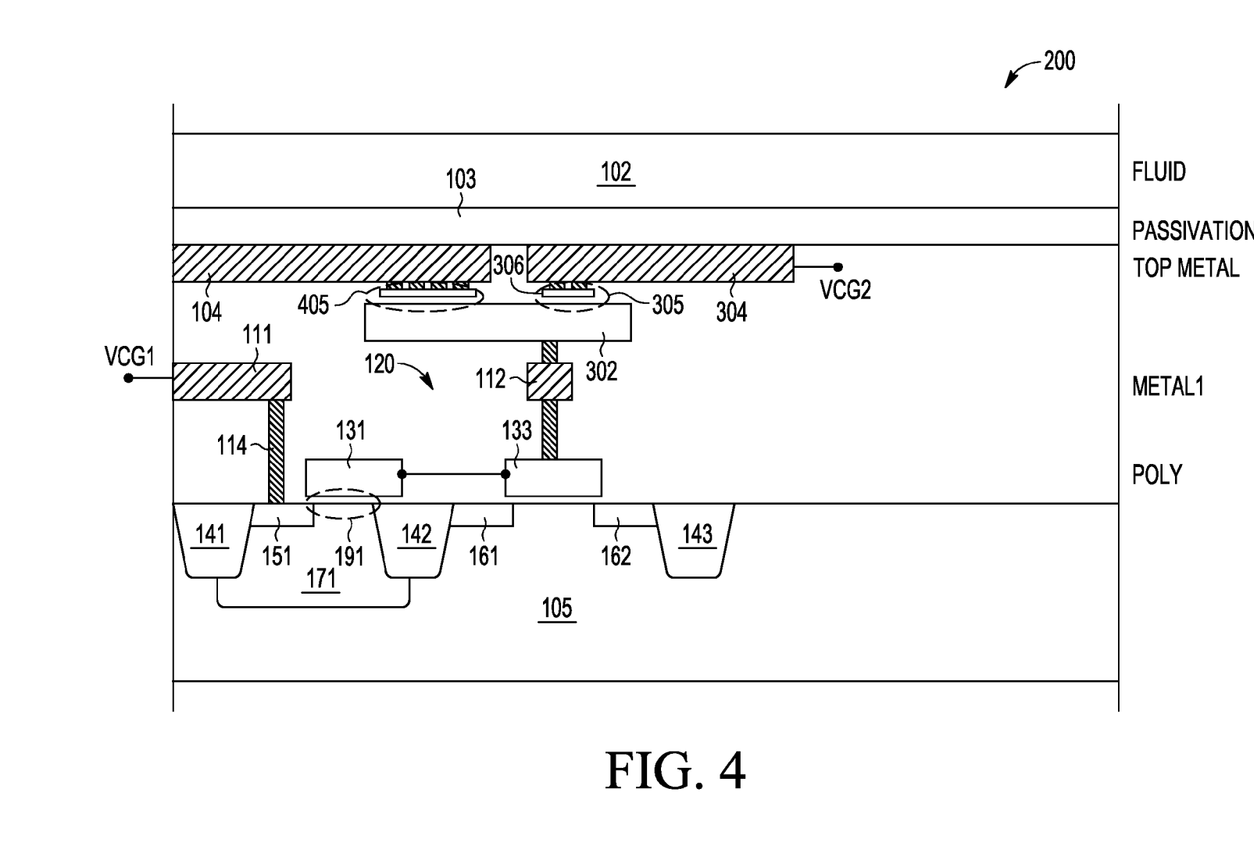
FIG. 4 is a conceptual cross-sectional view of an ISFET in accordance with an alternate embodiment of the invention.

FIG. 4 depicts yet another embodiment, wherein the top metal sensing plate is coupled to the floating gate via a MIM cap 405. In this embodiment VCG2 is coupled to metal structure 304, and VCG1 is coupled to control gate electrode 111. As with the embodiment shown in FIG. 2, only one poly-to-well capacitor 191 needs to be used.

Figure 5:
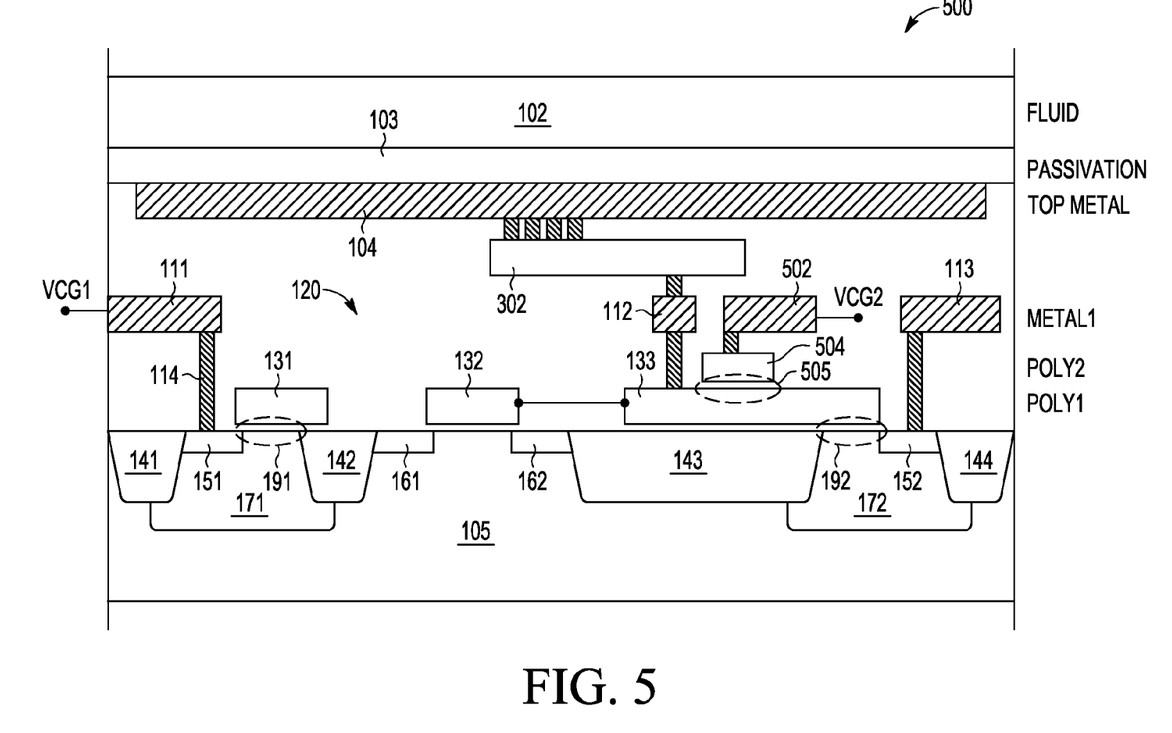
FIG. 5 is a conceptual cross-sectional view of an ISFET in accordance with an alternate embodiment of the invention.

FIG. 5 depicts a further embodiment, wherein a double-poly capacitor 505 is formed with respect to floating gate region 133. In this embodiment, poly-to-well capacitor 192 is optional, and need not be used. A bias on VCG2 is applied to a metal structure (metal1) 502 and poly2 structure 504 to effect trimming.

Figure 6:
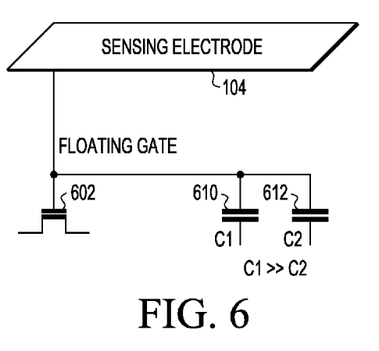
FIGS. 6-13 present schematic diagrams of various alternate embodiments of the invention.

FIGS. 6-13 depict, in schematic form, a variety of embodiments where the sensing and trimming occur through different combinations of capacitive and/or MOSFET structures. FIG. 6 depicts the case where sensing is provided through an NMOS FET 602 while tunneling through N-well poly-to-well capacitor 612 is used for trimming. In this embodiment, the capacitance of capacitor 610 is substantially larger than that of capacitor 612, and thus tunneling occurs within the smaller of the two capacitors.

Figure 7:
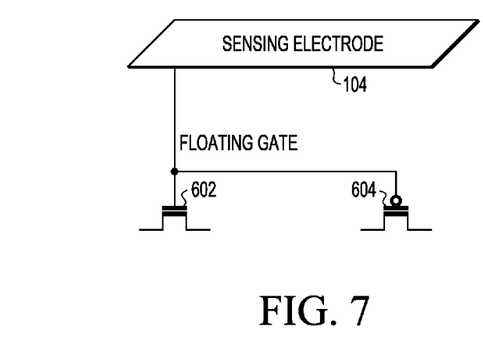
Figure 8:
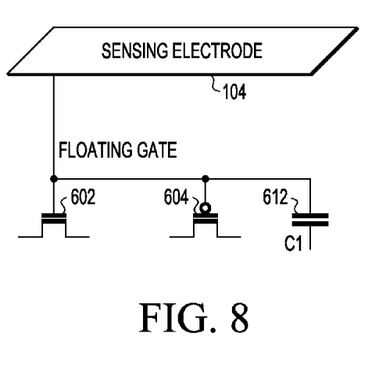
Figure 9:
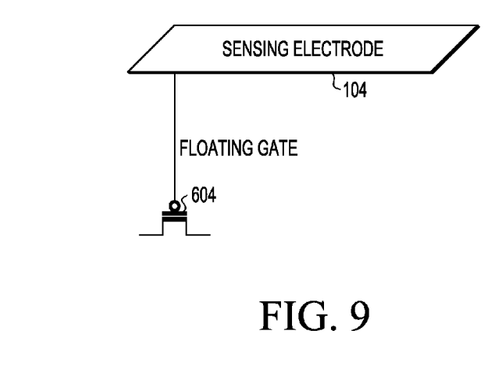
Figure 10:
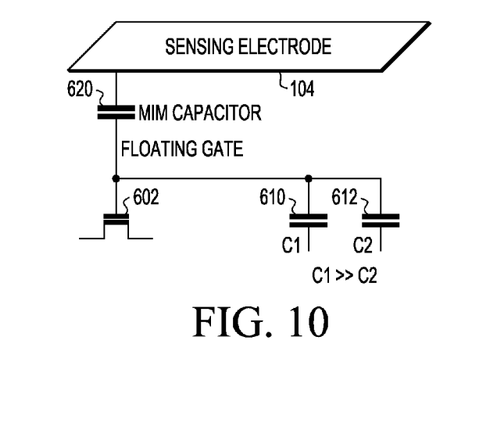
Figure 11:
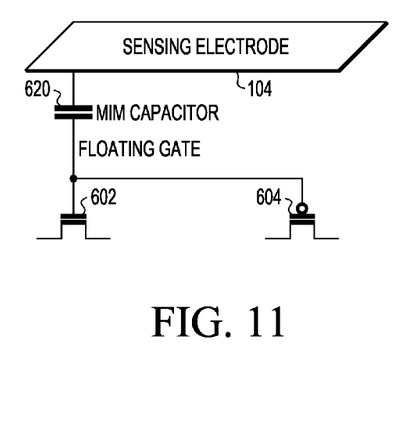
Figure 12:
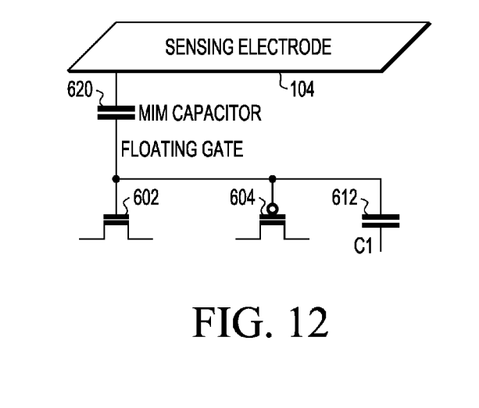
Figure 13:
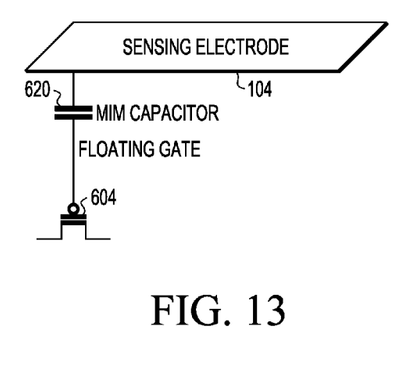

FIG. 7 depicts the case where sensing is performed through NMOS FET 602 while trimming is performed via tunneling and/or hot-carrier-injection (HCI) through a PMOS FET 604. A positive bias can be applied to the nwell of PMOS FET 604 to pull electrons off the floating gate by tunneling through the gate oxide of PMOS FET 604. On the other hand, a combination of bias can be applied to the source, drain and well of PMOS FET 604 to cause current flow through PMOS FET 604 and electrons injected on to the floating gate through the HCI mechanism. Similarly, FIG. 8 depicts the case where an additional N-well capacitor 610 is added to the topology shown in FIG. 7, such that capacitor 610 provides additional trimming capabilities by tunneling as in FIG. 6. FIG. 9 shows an embodiment where PMOS FET 604 is alone used for sensing as well as trimming via tunneling and hot-carrier-injection.

FIGS. 10-13 depict embodiments similar to those shown respectively in FIGS. 6-9; however, a MIM capacitor 620 is added between sensing electrode 104 and the remaining components. In these embodiments, the sensing and trimming are similar to those shown respectively in FIGS. 6-9. Although not shown in FIGS. 6-13, an optional additional MIM capacitor could be added to the structure to provide additional trimming capabilities similar to that shown in FIGS. 3 and 4.

The various embodiments described above may be produced using conventional semiconductor processing techniques, in particular, well-known CMOS techniques. Further, a variety of well known and common semiconductor materials may be used, i.e., traditional metals (aluminum, copper, gold, etc.), polysilicon, silicon dioxide, silicon nitride, silicon, and the like.

In general, what has been described is an ISFET structure including a substrate; a source region and a drain region formed within the substrate and having a channel region provided therebetween; a gate dielectric layer formed over the channel region; a floating gate structure formed on the gate dielectric over the channel region, the floating gate structure being electrically coupled to a first conductive structure configured to electrically communicate with a fluid having an ion concentration; and at least one control gate structure electrically coupled to the floating gate structure, the control gate structure configured to accept a voltage bias and to cause the movement of charge between the floating gate structure and the control gate structure in response to the voltage bias.

In one embodiment, at least one control gate structure comprises a control gate electrode and a capacitor structure formed by the substrate, the floating gate, and an oxide layer provided therebetween. The capacitor structure may be formed between the floating gate and a well provided within the substrate. In one embodiment, the control gate structure includes two control gates, each forming a respective capacitor in conjunction with the substrate. A further embodiment includes at least one metal-insulator-metal capacitor coupled between the floating gate structure and the first conductive structure. In one embodiment, the floating gate structure comprises polysilicon.

A method of trimming the threshold voltage of an ISFET having a floating gate and a control gate coupled thereto generally includes: determining a first threshold voltage value of the ISFET; applying a bias voltage to the control gate based on the first threshold voltage such that at least a portion of charge within the ISFET migrates to or from the control gate; adjusting the bias voltage until the ISFET has a second threshold voltage substantially equal to a predetermined threshold value; and removing the bias voltage from the control gate.

In one embodiment, the control gate includes a first control gate terminal and a second control gate terminal, and the trimming step includes applying a positive voltage to either the first control gate terminal or the second control gate terminal.

A CMOS ISFET in accordance with the present invention comprises a floating gate structure (e.g., a polysilicon structure) and a control gate structure communicatively coupled to the floating gate structure, wherein the control gate is configured to receive a bias voltage and effect transfer of charge selectively between the floating gate structure and the control gate structure. In one embodiment, the control gate structure comprises a control gate electrode and a capacitor structure formed by the substrate, the floating gate, and an oxide layer provided therebetween. In one embodiment, the capacitor structure is formed between the floating gate and a well provided within the substrate. In another embodiment, the control gate structure includes two control gates, each forming a respective capacitor with respect to the substrate. A further embodiment includes at least one metal-insulator-metal capacitor coupled between the floating gate structure and the first conductive structure. The floating gate structure may include a metal plate configured to sense an ion concentration of a fluid adjacent thereto.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An ISFET structure comprising:
   a substrate;
   a source region and a drain region formed within the substrate and having a channel region provided therebetween;
   a gate dielectric layer formed over the channel region;
   a floating gate structure formed on the gate dielectric over the channel region, the floating gate structure being electrically coupled to a first conductive structure configured to electrically communicate with a fluid having an ion concentration; and
   at least one control gate structure formed at least partially in the substrate and electrically coupled to the floating gate structure, the control gate structure configured to accept a voltage bias and to cause the movement of charge between the floating gate structure and the control gate structure in response to the voltage bias;
   wherein the at least one control gate structure comprises a control gate electrode coupled to the substrate via a conductive interconnect, and a capacitor structure formed by the substrate, the floating gate, and an oxide layer provided therebetween.

2. The ISFET structure of claim 1, wherein the capacitor structure is formed between the floating gate and a well provided within the substrate.

3. The ISFET structure of 1, wherein the at least one control gate structure includes two control gates, each coupled to a respective capacitor structure formed by the substrate, the floating gate, and an oxide layer provided therebetween.

4. The ISFET structure of claim 1, further including at least one metal-insulator-metal capacitor coupled between the floating gate structure and the first conductive structure.

5. The ISFET structure of claim 1, wherein the floating gate structure comprises polysilicon.

* * * * *